(12) United States Patent
Stroelin

(10) Patent No.: US 12,200,842 B2
(45) Date of Patent: Jan. 14, 2025

(54) SYSTEM FOR MONITORING A SURGICAL LUMINAIRE ASSEMBLY

(71) Applicant: KARL LEIBINGER MEDIZINTECHNIK GMBH & CO. KG, Muehlheim (DE)

(72) Inventor: Joachim Stroelin, Rietheim-Weilheim (DE)

(73) Assignee: KARL LEIBINGER ASSET MANAGEMENT GMBH & CO. KG., Mühlheim an der Donau (DE)

(*) Notice: Subject to any disclaimer, the term of this patent is extended or adjusted under 35 U.S.C. 154(b) by 155 days.

(21) Appl. No.: 18/000,269

(22) PCT Filed: May 27, 2021

(86) PCT No.: PCT/EP2021/064202
§ 371 (c)(1),
(2) Date: Nov. 29, 2022

(87) PCT Pub. No.: WO2021/239873
PCT Pub. Date: Dec. 2, 2021

(65) Prior Publication Data
US 2023/0225034 A1    Jul. 13, 2023

(30) Foreign Application Priority Data
May 29, 2020  (DE) ..................... 10 2020 114 416.4

(51) Int. Cl.
*H05B 47/115* (2020.01)
*A61B 90/35* (2016.01)
(Continued)

(52) U.S. Cl.
CPC ............ *H05B 47/115* (2020.01); *A61B 90/35* (2016.02); *F21V 21/26* (2013.01); *F21W 2131/205* (2013.01)

(58) Field of Classification Search
CPC .................. H05B 47/115; A61B 90/35; A61B 2017/00398; A61B 2034/2055; A61B 90/30; F21V 21/26; F21W 2131/205
See application file for complete search history.

(56) References Cited

U.S. PATENT DOCUMENTS

2005/0195587 A1* 9/2005 Moctezuma De La Barrera ........ A61B 90/30 362/5
2011/0037840 A1* 2/2011 Hiltl ....................... A61B 90/35 348/61

(Continued)

FOREIGN PATENT DOCUMENTS

CA    2635954 A1 *  7/2007  ............. G06F 16/00
DE   10225077 A1    12/2003

(Continued)

OTHER PUBLICATIONS

ISA European Patent Office, International Search Report Issued in Application No. PCT/EP2021/064202, Aug. 25, 2021, WIPO, 6 pages.

*Primary Examiner* — Abdullah A Riyami
*Assistant Examiner* — Syed M Kaiser
(74) *Attorney, Agent, or Firm* — McCoy Russell LLP

(57) ABSTRACT

The present invention relates to a system for monitoring a surgical luminaire assembly comprising at least one surgical luminaire, with a monitoring unit. It is provided here that the system comprises a 3D sensor which three-dimensionally detects the surgical luminaire assembly and/or an operating area arranged below the surgical luminaire assembly, wherein the data of the 3D sensor are evaluated by the monitoring unit with respect to the surgical luminaire assembly.

20 Claims, 2 Drawing Sheets

(51) Int. Cl.
*F21V 21/26* (2006.01)
*F21W 131/205* (2006.01)

(56) References Cited

U.S. PATENT DOCUMENTS

| | | | |
|---|---|---|---|
| 2013/0226344 A1* | 8/2013 | Wong | G05D 1/0242 |
| | | | 901/1 |
| 2017/0154158 A1* | 6/2017 | Marka | G05B 19/048 |
| 2017/0318644 A1 | 11/2017 | Hartl et al. | |
| 2019/0249847 A1* | 8/2019 | Hallack | A61B 90/30 |

FOREIGN PATENT DOCUMENTS

| | | | |
|---|---|---|---|
| DE | 102007028731 A1 | 1/2009 | |
| DE | 102009037316 A1 | 2/2011 | |
| DE | 102014212632 A1 | 12/2015 | |
| DE | 102014222794 A1 | 5/2016 | |
| DE | 102016117067 A1 | 3/2018 | |
| EP | 1728482 A1 | 12/2006 | |
| KR | 20190126331 A * | 11/2019 | ......... G06F 3/04815 |
| WO | 2012117108 A1 | 9/2012 | |
| WO | 2020077562 A1 | 4/2020 | |

\* cited by examiner

SYSTEM FOR MONITORING A SURGICAL LUMINAIRE ASSEMBLY

CROSS REFERENCE TO RELATED APPLICATIONS

The present application is a U.S. National Phase of International Application No. PCT/EP2021/064202 entitled "SYSTEM FOR MONITORING AN OPERATING LIGHT ASSEMBLY," and filed on May 27, 2021. International Application No. PCT/EP2021/064202 claims priority to German Patent Application No. 10 2020 114 416.4 filed on May 29, 2020. The entire contents of each of the above-listed applications are hereby incorporated by reference for all purposes.

TECHNICAL FIELD

The present invention relates to the operation of a surgical luminaire assembly comprising at least one surgical luminaire or at least two surgical luminaires.

BACKGROUND AND SUMMARY

In an operating theatre, in most cases, in addition to the surgical luminaire assembly, which is usually mounted on the ceiling via a support system, many other devices are provided, some of which are also mounted on the ceiling, and some of which are located in the area below the surgical luminaire assembly. In addition, there are usually multiple persons of surgical staff.

Collisions occur repeatedly and regularly when positioning the surgical luminaires or other devices. On the one hand, the collisions prevent the desired positioning and, on the other hand, the collisions can cause damage to the devices. This can be quite critical if, over a longer period of time, the damage causes paint to flake off and fall off. In the case of massive collisions, parts can come loose or even arms can break.

The operating theatre is not usually equipped with sensors. At most, there is a normal room camera or cameras in the surgical luminaires to document an operation. Furthermore, there are navigation systems to position the instruments and their direction during difficult or complex operations.

Document DE 10 2007 028 731 A1 discloses a method in which three-dimensional image data of an operating theatre are captured and objects/devices are separated in order to determine movement sequences from the available and assignable data sets and to intervene in operating functions in a controlling manner.

Document DE 10 2014 212 632 A1 shows a method for monitoring the operation of a medical device. In particular, the configuration of an operating table is determined via a 3D sensor and transferred into a kinematic model of the operating table.

It is an object of the present invention to provide a system that allows safer and/or simpler operation of the surgical luminaire assembly.

This object is achieved by a system for monitoring a surgical luminaire assembly according to claim 1. Preferred embodiments of the present invention are the subject-matter of the dependent claims.

The present invention comprises a system for monitoring a surgical luminaire assembly comprising at least one surgical luminaire, with a monitoring unit. The invention is characterized in that the system comprises a 3D sensor which three-dimensionally captures the surgical luminaire assembly and/or an operating area arranged below the surgical luminaire assembly, wherein the data of the 3D sensor are evaluated by the monitoring unit with respect to the surgical luminaire assembly.

In one possible embodiment of the present invention, the at least one surgical luminaire is arranged on a support system, wherein the 3D sensor is arranged on the support system. This allows for a particularly good capture of the relevant events.

In one possible embodiment of the present invention, the 3D sensor is arranged on a central shaft of the support system, in particular at a lower end of the central shaft.

In one possible embodiment of the present invention, the support system comprises a plurality of support arms rotatably mounted on the central shaft, with the at least one surgical luminaire and/or monitors and/or a ceiling supply unit being arranged on the support arms.

In one possible embodiment of the present invention, the 3D sensor monitors an angular range of 360°. For example, it can be embodied as a 360° scanner or as a sensor with 360° optics.

In one possible embodiment of the present invention, a center axis of the observation area of the 3D sensor is directed vertically downwards.

In one possible embodiment of the present invention, the 3D sensor comprises a plurality of sensor elements which are arranged at different positions in the room, in particular on the ceiling and/or on one or more walls of the operating theatre. This also allows a good capture of events. Preferably, the sensors are directed obliquely downwards.

In one possible embodiment of the present invention, the monitoring unit generates actuating information for the surgical luminaire assembly by evaluating the data of the 3D sensor.

In a first variant, the actuating information can be constituted by control commands via which the monitoring unit controls the surgical luminaire assembly.

In a second variant, the actuating information is output to an operator on an output device. The operator can thus change and/or adapt the operation and/or control of the at least one surgical luminaire on the basis of the actuating information.

The output device can output the actuating information visually and/or acoustically, for example. In particular, the actuating information can be shown on a display.

In one possible embodiment, the actuating information can comprise warnings and/or instructions for the orientation and/or positioning of the at least one surgical luminaire.

In one possible embodiment of the present invention, the monitoring unit recognizes one or more persons located in an operating area arranged below the surgical luminaire assembly by evaluating the data of the 3D sensor.

In one possible embodiment of the present invention, the monitoring unit generates actuating information for the surgical luminaire assembly depending on the position of the at least one person.

In one possible embodiment of the present invention, the monitoring unit detects the position of a patient and/or an operating table and generates actuating information for orienting the one or more surgical luminaires of the surgical luminaire assembly towards a surgical field of the patient.

In one possible embodiment of the present invention, the actuating information is constituted by control commands and/or information regarding the joint orientation of the light fields of a plurality of surgical luminaires towards the surgical field.

In one possible embodiment of the present invention, the monitoring unit determines the height and/or position at which the patient and/or the surgical field is located relative to the at least one surgical luminaire, wherein preferably the actuating information is generated as a function of the height and/or position.

In one possible embodiment of the present invention, the monitoring unit detects the position of one or more surgeons and generates actuating information regarding an orientation of the one or more surgical luminaires of the surgical luminaire assembly, by which they are directed towards a surgical field of the patient between the surgeons and/or shadowing is avoided.

In one possible embodiment of the present invention, one or more predefined scenarios of an arrangement of surgeons and surgical luminaires arranged relative to them can be stored in the monitoring unit, wherein the monitoring unit preferably generates the actuating information by matching the position of the surgeons with the one or more predefined scenarios.

In one possible embodiment of the present invention, the at least one surgical luminaire is arranged on a support system adjustable via one or more drives, wherein the monitoring unit generates control commands for controlling the one or more drives in order to arrange and/or orient the at least one surgical luminaire.

In one possible embodiment of the present invention, the monitoring unit detects the position of the at least one surgical luminaire and/or support arms of a support system of the at least one surgical luminaire and/or other devices located in the operating area by evaluating the signals from the 3D sensor.

In one possible embodiment of the present invention, the monitoring unit performs collision monitoring.

In one possible embodiment of the present invention, the support system and/or one or more of the devices comprises actuators by which a movement can be slowed down and/or changed, wherein the collision monitoring actuates the actuator or actuators when a possible collision is recognized. In particular, the actuator(s) may be drives and/or brakes.

In one possible embodiment of the present invention, the monitoring unit monitors the position and/or orientation of the surgical luminaire assembly with respect to the function of a ventilation ceiling. The ventilation ceiling may be positioned above the luminaire assembly and/or the operating table and may generate a flow of purified cooled air which descends onto the operating area and prevents contaminated air from entering the operating area. However, the laminar flow necessary for this can be considerably impaired by unfavorable positioning of the surgical luminaire or surgical luminaires.

In one possible embodiment of the present invention, the system provides a warning when the function of the ventilation ceiling is impaired.

In one possible embodiment of the present invention, the monitoring unit changes the position and/or orientation of the surgical luminaire assembly when the function of the ventilation ceiling is impaired.

In one possible embodiment of the present invention, the system controls the ventilation ceiling as a function of the position and/or orientation of the surgical luminaire assembly, in particular to maintain the function of the ventilation ceiling despite the position and/or orientation of the luminaire assembly.

In one possible embodiment of the present invention, the surgical luminaire assembly comprises at least two luminaires.

In one possible embodiment of the present invention, the monitoring unit detects the relative orientation of the light axes of the luminaires in relation to each other and/or to a patient.

In one possible embodiment of the present invention, navigation points are arranged on the at least one surgical luminaire and/or a support system for the at least one surgical luminaire, the position of said navigation points being detected by the 3D sensor. In particular, these may be optical markers. The optical markers may be coded and/or uncoded.

In one possible embodiment of the present invention, the monitoring unit comprises a microcontroller and software which is stored on a non-volatile memory and which runs on the microcontroller to implement the functions described above. For this purpose, the monitoring unit is connected to the 3D scanner to receive and evaluate signals from the 3D scanner. Furthermore, the monitoring unit can be connected to input and/or output elements and/or a controller of the system.

Furthermore, in one possible embodiment of the present invention, the system comprises a controller comprising a microcontroller and software which is stored on a non-volatile memory and which runs on the microcontroller to implement the actuating functions described above.

The monitoring unit can be integrated into the controller or formed separately therefrom.

The present invention further comprises an examination luminaire assembly comprising at least one luminaire and a system as described above.

The present invention will now be explained in greater detail on the basis of drawings and exemplary embodiments.

DETAILED DESCRIPTION

Figure 1:
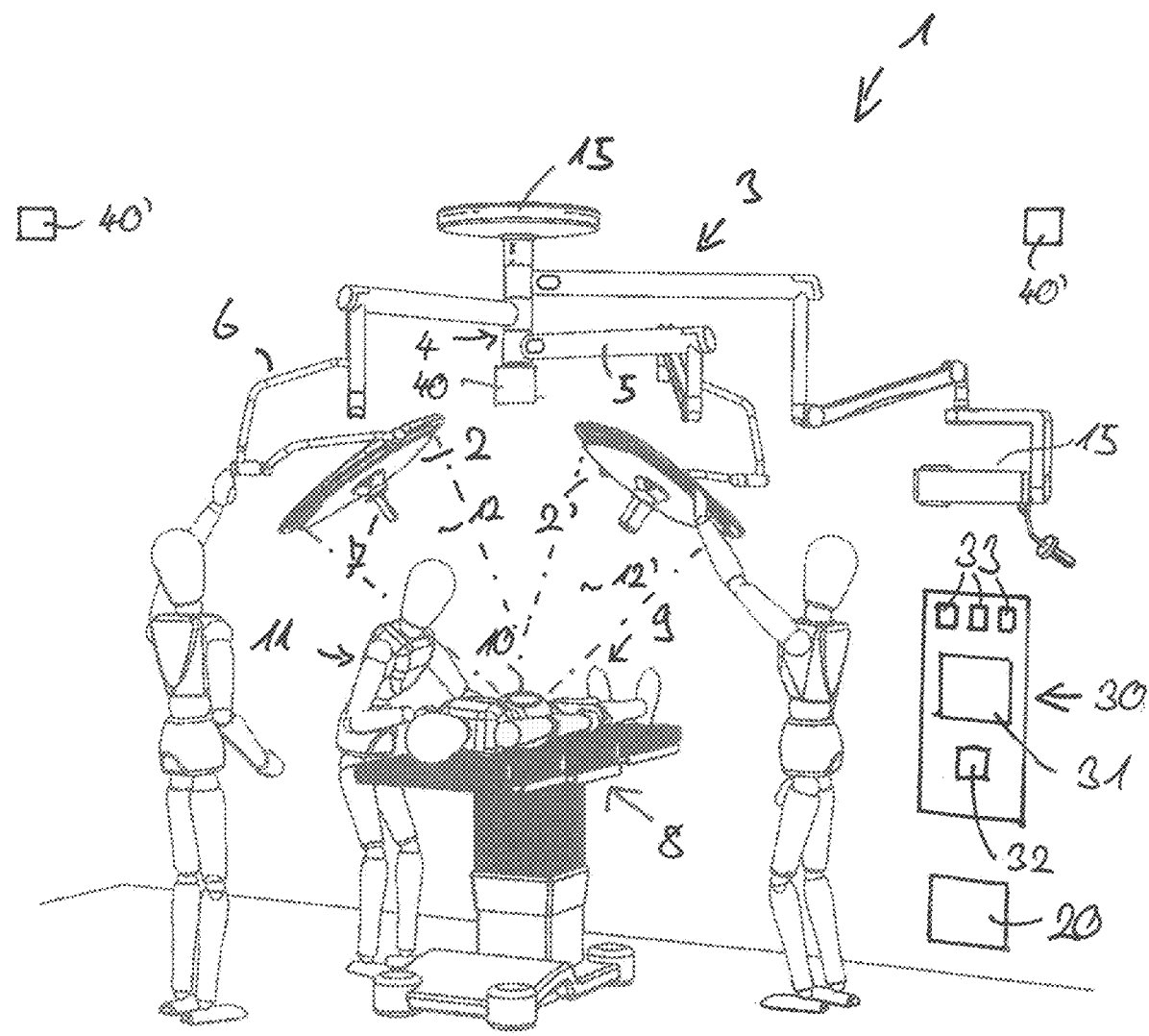
FIG. 1 shows a first exemplary embodiment of a surgical luminaire assembly according to the invention with a monitoring unit according to the invention and FIG. 2 shows a second exemplary embodiment of a surgical luminaire assembly according to the invention with a monitoring unit according to the invention.

FIG. 1 shows an exemplary embodiment of a surgical luminaire assembly 1 according to the invention with a first surgical luminaire 2 and a second surgical luminaire 2'. However, within the scope of the present invention, the surgical luminaire assembly 1 could also comprise only one surgical luminaire or more than two surgical luminaires.

In the exemplary embodiment, the surgical luminaires 2 and 2' are arranged adjustable in their position and orientation via a support system 3 above an operating table 8. The adjustment is usually done by hand. However, adjustment by means of drives of the support system 3 is also conceivable. In the exemplary embodiment, the support system comprises a ceiling mount 15, via which a central shaft 4 is mounted on the ceiling. Support arms 5 are pivotably arranged on the central shaft 4. The surgical luminaires 2 and 2' are each arranged on different support arms 5 via further support arm elements 6 and joints, and have a handle 7 on which they can be moved. However, other designs of the support system are also conceivable.

The surgical luminaires 2 and 2' each generate a light field 12 and 12' respectively with a light axis 13 and 13' respectively. By arranging and orienting the surgical luminaires 2 and 2' accordingly, the light fields 12 and 12' can be directed towards a surgical field 10 of the patient 9 lying on the operating table 8 so that they overlap. In other cases, however, the two light fields 12 and 12' of the surgical luminaires 2 and 2' can also be directed towards different areas. For example, in the context of a transplantation, one surgical luminaire can be directed towards the surgical field 10 of the patient 9 lying on the operating table 8, and another surgical luminaire can be directed towards the transplant.

FIG. 1 shows a control apparatus 30 via which functions of the surgical luminaires 2 and 2' can be controlled, in particular brightness adjustment and/or light field size and/or color temperature and/or switching on and off. In the exemplary embodiment shown, this control apparatus is mounted on a wall. Alternatively, the control apparatus 30 could also be embodied as a table or mobile version. The control apparatus preferably has input elements 33, for example in the form of switches, actuators and/or a touchscreen. Furthermore, the control apparatus 30 preferably comprises a display 31 on which operating states and/or current setting parameters of the individual surgical luminaires 2 and 2' can be displayed.

The surgical luminaires 2 and 2' can be networked with each other and/or with a common controller and/or operating unit by cable and/or wirelessly. Via this communication, it is preferably possible to control and/or synchronize functions of the surgical luminaires 2 and 2', such as brightness adjustment, focus adjustment or color temperature, as well as simultaneous switching on and off.

Figure 2:
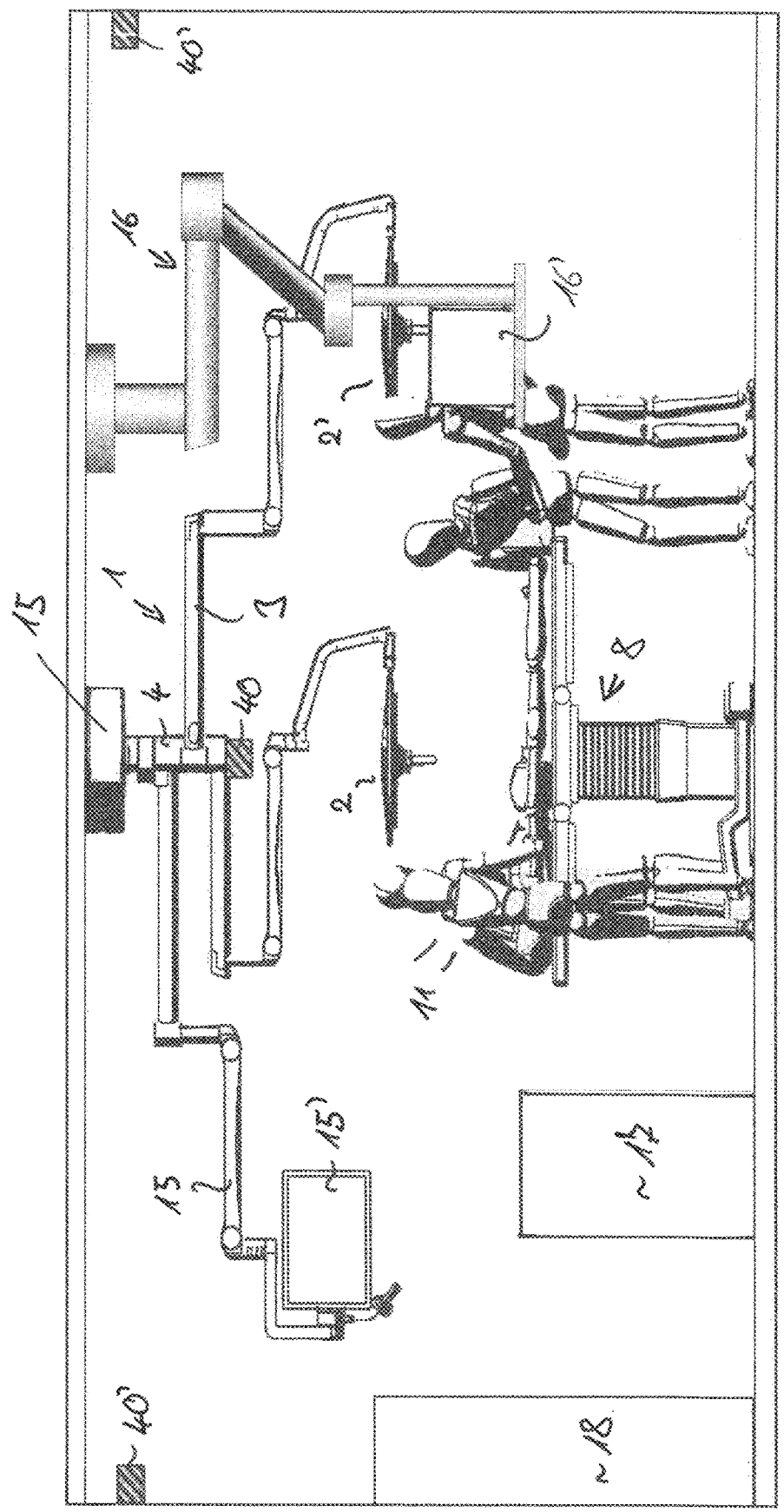

Furthermore, as shown in part in the exemplary embodiment in FIG. 2, one or more of the following devices may be located in the operating theatre: anesthesia station, monitor suspension means 15 for monitors 15', supply systems 16' (CSU=ceiling supply unit) with electrical and gas connections (1-2 pieces per operating theatre) and/or their support systems 16, various equipment trolleys 18, one or more instrument tables 17, stools, steps, infusion stands, endoscopy trolleys, monitor trolleys.

According to the invention, the surgical luminaire assembly comprises a monitoring unit 20, which is only shown symbolically here. This can be part of a controller of the surgical luminaires, integrated therein and/or external thereto, and/or of the control apparatus 11.

Furthermore, a 3D sensor 40, 40', which is also shown only schematically, is provided, which three-dimensionally captures the surgical luminaire assembly and/or an operating area arranged below the surgical luminaire assembly, wherein the data of the 3D sensor are evaluated by the monitoring unit 20 with respect to the surgical luminaire assembly.

As can be seen in FIGS. 1 and 2, in a first variant of the invention, the 3D sensor 40 can be arranged on the support system 3 of the surgical luminaires 2, 2', in particular at the lower end of the central shaft 4. In a second variant, sensor elements 40' of the 3D sensor are arranged on the ceiling or the walls of the operating theatre.

In one possible embodiment of the present invention, the 3D sensor monitors the positions of all objects and/or persons in the operating theatre at all times. The 3D sensor provides a 3D map of the room.

The 3D sensor or its one or more sensor elements 40, 40' are located at suitable positions for this purpose and have suitable fields of view.

In a first variant, a 360° sensor 40, for example a rotating 360° scanner or a sensor with 360° optics, is located in a central position. The lower position on the central bearing shaft 4 of the surgical luminaire support system 3 is an ideal position for a single 360° sensor 40.

In a second variant, a plurality of sensor elements 40' are used, which for example have a fixed field of view and/or a field of view encompassing less than 360°, and which are arranged for example in the corners of the room or on the walls.

There are different types of 3D sensors, all of which can be used within the scope of the invention. For example, the 3D sensor can be one or more laser scanners or optical, camera-based sensors, which work photogrammetrically, for example.

The monitoring unit 20 generates a 3D model from the data of the 3D sensor. For this purpose, the monitoring unit 20 has a computer for evaluating the data. Ideally, all devices are networked with this computer.

Numerous functions can be derived from the information of the 3D sensor. Preferably, the monitoring unit evaluates the information with regard to the settings and/or positions of the surgical luminaires 2 and 2'.

In one possible embodiment of the present invention, the computer analyses the data and calculates the best possible settings and/or positions of the surgical luminaires 2 and 2' and possibly other devices. These settings and/or positions can be shown on a display 31 of the control apparatus 30. Alternatively or additionally, the support system 3 and/or the devices, can be controlled by the monitoring unit to make the settings and/or assume the optimal positions.

In particular, surgical luminaires which are arranged on a support system with driven arms, booms and/or joints can assume an optimum position through the control by means of the monitoring unit and can thus be positioned between the surgeons 11 with the best possible orientation towards the surgical field 10, so that no shadows are created. Furthermore, an optimal position can be displayed.

The monitoring unit may be configured to recognize when the surgeon 11 repositions himself and then to reposition the surgical luminaire.

In one possible embodiment of the present invention, the monitoring unit 20 uses the information from the 3D sensor to determine where and at what height the operating table with patient is and at what distance therefrom the surgical luminaire(s) 2, 2' is/are located. Preferably, the monitoring unit uses this information to determine an orientation and/or control of the surgical luminaire(s), by means of which they are optimally focused on the surgical field 10.

In one possible embodiment of the present invention, predefined scenarios are stored in the monitoring unit and are approached depending on the sensor data, for example predefined scenarios for different surgical disciplines. For example, a scenario could be defined as follows: 3 persons present. These are detected, and the operating table 8 and the surgical luminaires 2, 2' are arranged in an associated predefined position and corresponding parameters are preset at all devices.

In one possible embodiment of the present invention, the monitoring unit 20 is configured to warn of collisions. Alternatively or additionally, the support system 3 and/or the devices may have brakes and/or drives, wherein the monitoring unit stops the drives and/or applies the brakes to avoid collisions.

In a possible embodiment of the present invention, the monitoring unit uses the information determined by the sensor unit to optimally adjust a ventilation ceiling arranged on the ceiling above the operating table, or issues notifications if the function of the ventilation ceiling is disturbed, for example, by an unfavorable positioning of the surgical luminaires 2, 2' and/or a large obstacle.

The invention claimed is:

1. A system for monitoring a surgical luminaire assembly comprising at least one surgical luminaire, with a monitoring unit,
wherein
the system comprises a 3D sensor which three-dimensionally captures the surgical luminaire assembly and/or an operating area arranged below the surgical luminaire assembly, wherein the data of the 3D sensor are evaluated by the monitoring unit with respect to the surgical luminaire assembly,
wherein the at least one surgical luminaire is arranged on a support system, wherein the 3D sensor is arranged on the support system separately from the at least one surgical luminaire.

2. The system according to claim 1, wherein the 3D sensor monitors an angular range of 360°.

3. The system according to claim 1, wherein the 3D sensor comprises a plurality of sensor elements which are arranged at different positions in a room.

4. The system according to claim 1, wherein the monitoring unit generates actuating information for the surgical luminaire assembly by evaluating the data of the 3D sensor.

5. The system according to claim 1, wherein the monitoring unit recognizes one or more persons located in an operating area arranged below the surgical luminaire assembly by evaluating the data of the 3D sensor and generates actuating information for the surgical luminaire assembly depending on the position of the at least one person.

6. The system according to claim 5, wherein the monitoring unit detects the position of a patient and/or an operating table and generates actuating information for orienting the at least one surgical luminaire of the surgical luminaire assembly towards a surgical field of the patient.

7. The system according to claim 6, wherein the monitoring unit detects the position of one or more surgeons and generates actuating information regarding an orientation of the at least one surgical luminaire of the surgical luminaire assembly, by which they are directed towards a surgical field of the patient between the surgeons and/or shadowing is avoided.

8. The system according to claim 7, wherein one or more predefined scenarios of an arrangement of surgeons and surgical luminaires arranged relative to them can be stored in the monitoring unit, wherein the monitoring unit generates the actuating information by matching the position of the surgeons with the one or more predefined scenarios.

9. The system according to claim 1, wherein the at least one surgical luminaire is arranged on the support system adjustable via one or more drives, wherein the monitoring unit generates control commands for controlling the one or more drives in order to arrange and/or orient the at least one surgical luminaire.

10. The system according to claim 1, wherein the monitoring unit detects the position of the at least one surgical luminaire and/or support arms of the support system of the at least one surgical luminaire and/or other devices located in the operating area by evaluating the signals from the 3D sensor.

11. The system according to claim 10, wherein the monitoring unit performs collision monitoring.

12. The system according to claim 1, wherein the surgical luminaire assembly comprises at least two luminaires, and wherein the monitoring unit detects the relative orientation of the light axes of the luminaires in relation to each other and/or to a patient, and/or wherein navigation points are arranged on the at least one surgical luminaire and/or the support system for the at least one surgical luminaire, the position of said navigation points being detected by the 3D sensor.

13. An examination luminaire assembly, comprising at least one luminaire and a system according to claim 1.

14. The system according to claim 1, wherein the 3D sensor is arranged on the support system on a central shaft of the support system, at a lower end of the central shaft.

15. The system according to claim 4, wherein the actuating information is constituted by control commands via which the monitoring unit controls the surgical luminaire assembly, and/or wherein the actuating information is output to an operator on an output device, wherein the actuating information is further shown on a display and/or comprises warnings and/or instructions for the orientation and/or positioning of the at least one surgical luminaire.

16. The system according to claim 5, wherein the monitoring unit detects the position of a patient and/or an operating table and generates actuating information for orienting the at least one surgical luminaire of the surgical luminaire assembly towards a surgical field of the patient, for jointly orienting the light fields of a plurality of surgical luminaires towards the surgical field, for which purpose the monitoring unit determines the height and/or position at which the patient and/or the surgical field is located relative to the at least one surgical luminaire.

17. The system according to claim 11, wherein the support system and/or one or more of the devices comprises actuators by which a movement can be slowed down and/or changed, wherein the collision monitoring actuates the actuator or actuators when a possible collision is recognized.

18. The system according to claim 14, wherein the support system comprises at least one support arm rotatably mounted on the central shaft, with the at least one surgical luminaire being arranged on the at least one support arm.

19. A system for monitoring a surgical luminaire assembly comprising at least one surgical luminaire, with a monitoring unit,
wherein the system comprises a 3D sensor which three-dimensionally captures the surgical luminaire assembly and/or an operating area arranged below the surgical luminaire assembly, wherein the data of the 3D sensor are evaluated by the monitoring unit with respect to the surgical luminaire assembly, and
wherein the monitoring unit monitors the position and/or orientation of the surgical luminaire assembly with respect to the function of a ventilation ceiling.

20. The system according to claim 19, wherein the monitoring unit monitors the position and/or orientation of the surgical luminaire assembly with respect to the function of a ventilation ceiling and provides a warning and/or changes the position and/or orientation of the surgical luminaire assembly when this function is impaired and/or actuates the ventilation ceiling as a function of the position and/or orientation of the surgical luminaire assembly.

* * * * *